US006245540B1

(12) United States Patent
Hudson et al.

(10) Patent No.: US 6,245,540 B1
(45) Date of Patent: *Jun. 12, 2001

(54) HUMAN CHOLINE ACETYLTRANSFERASE

(75) Inventors: Peter J. Hudson, Rockville; Wei Wu He, Columbia; Craig A. Rosen, Laytonsville; Jeannine D. Gocayne, Potomac, all of MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/464,601

(22) Filed: Jun. 5, 1995

Related U.S. Application Data

(63) Continuation-in-part of application No. PCT/US94/13570, filed on Nov. 23, 1994.

(51) Int. Cl.[7] .............................. C12N 9/10; C12N 15/54; C12N 15/63
(52) U.S. Cl. ........................ 435/193; 435/6; 435/252.3; 435/254.11; 435/325; 435/320.1; 536/23.2; 536/23.4; 536/24.3
(58) Field of Search .............................. 435/69.1, 320.1, 435/172.3, 193; 536/23.2, 23.5

(56) References Cited

U.S. PATENT DOCUMENTS 5,278,045   1/1994  Tam ..................................... 435/7.8

OTHER PUBLICATIONS

Corti et al. (1994) Molecular Cloning of cDNAs Encoding Human Carnitine Acetyltransferase and Mapping of the Corresponding Gene to Chromosome 9q34.1 Genomics 23(1): 94–99.*

Corti et al. *H.sapiens* mRNA for carnitine acetyltransferase, Genbank accession number X78706, submitted Apr. 8, 1994.*

Esser et al. (1993) Cloning, Sequencing, and Expression of a cDNA Encoding Rat Liver Carnitine Palmitoyltransferase. J. Biol. Chem. 268(8): 5817–5822.*

PCT International Search Report for PCT/US94/13570.

Salvaterra, Paul M.; Molecular Neurobiology; vol. 1, 1987; pp. 247–280.

Ostermann–Latif et al.: Journal of Neurochemistry; 1992; vol. 58; pp. 1060–1065.

Roskoski, Jr. et al.; Biochemistry vol. 14, No. 23; 1975; pp. 5105–5110.

Oda et al.; Molecular Brain Research, 16 (1992) 287–294; pp. 3–10.

Lorenzi et al.; DNA and Cell Biology, vol. 11, No. 8, 1992, pp. 593–603.

Mallet et al.; Progress in Brain Research, vol. 84; 1990.

Fann et al.; J. Neurochem. 61, 1349–1355; 1993.

Li et al.; Journal of Neurochemistry, 61, 748–751; 1993.

Berrard et al.; Brain Research Bulletin, vol. 22, pp. 147–153; 1989.

McGeer et al., Life Sciences, 34:2319–2338 (1984).

Strauss et al., Soc. For Neuroscience Abstracts, 11(2):1114 (1985).

Hersh et al., Klinische Pharmakologie, 2:15–19 (1989).

* cited by examiner

*Primary Examiner*—Lisa Hobbs
(74) *Attorney, Agent, or Firm*—Human Genome Sciences, Inc.

(57) ABSTRACT

Human choline acetyltransferase polypeptide and DNA (RNA) encoding such polypeptide and a procedure for producing such polypeptide by recombinant techniques is disclosed. Also disclosed are methods for utilizing such polypeptide for the treatment of cognitive and neurological deficiencies or mental disturbances such as degenerative nervous system disorders, for example, Alzheimer's Disease, ALS and other cholinergic defects, and antagonists for treating Parkinson's Disease and other disorders relating to an over-expression of acetylcholine. Also disclosed are diagnostic methods for detecting a mutation in the human Choline Acetyltransferase nucleic acid sequence.

56 Claims, 4 Drawing Sheets

FIG. 1A

```
  1  ATG AAG GCT TCC AGC CGC TTC AAG CAC CAG GAT GCA CTG CCA CGG TTG CCC
       M   K   A   S   S   R   F   K   H   Q   D   A   L   P   R   L   P
 55  GTG CCC CCT CTC CAG GAG TAC CTG AAG GCG CTG CAG CCC ATC
       V   P   P   L   Q   E   Y   L   K   A   L   Q   P   I
109  GTG AGT GAG GAG GTA GGG GAT GTG CTG GAT GAG TTT CAG GCC
       V   S   E   E   V   G   D   V   L   D   E   F   Q   A
163  TCA GGA GGT AAC GTA CGC CAC CTG CAG CGT CGG CCC AGG AAG
       S   G   G   N   V   R   H   L   Q   R   R   P   R   K
217  ACG GAG AAC TGG CTG TCT GAG CTC AAG ACC TAC CTC TAC CGC
       T   E   N   W   L   S   E   L   K   T   Y   L   Y   R
271  CAG CCT GTC GTC ATC TAC TCG AGC CCA ATG CTA CCC AAG GAC TTC
       Q   P   V   V   I   Y   S   S   P   M   L   P   K   D   F
325  GTG GAC CTG CAG GGT CAG CTC CGA TTT GCT GCC ATT CTC AAG GGT CTG GGG
       V   D   L   Q   G   Q   L   R   F   A   A   I   L   K   G   L   G
379  GTT TTC AAG GTC ATG GAT AAC GAG TTC TAT TAT CAG CTG CTG CTG TAC CGA
       V   F   K   V   M   D   N   E   F   Y   Q   L   P   V   E   Y   L
433  AAG CCA CTG TGC ATG AAC CAG TTC AAC GTC AGC TTC AGG ACC AAG AAG CCG
       K   P   L   C   M   N   Q   F   N   V   S   F   S   T   K   K   P
487  GGC CCC AAG CAG GAC ACA GTC TAC AAC TAC TTT TTT CCT CCC ACG
       G   P   K   Q   D   T   V   Y   N   Y   F   F   P   P   T
541  CAC ATC ACC GTG GTA CAC AAC TAC CAG TTT TTT GAG CTG GAT GTG TAC CAC AGT
       H   I   T   V   V   H   N   Y   Q   F   F   E   L   D   V   Y   H   S
```

MATCH WITH FIG. 1B

FIG. 1B

MATCH WITH FIG. 1A

| | | | | | | | | | | | | | | | | | |
|---|---|---|---|---|---|---|---|---|---|---|---|---|---|---|---|---|---|
| | H | I | T | V | V | H | N | Y | Q | F | F | E | L | D | V | Y | H | S |
| 595 | GAC | GGG | ACA | CCC | CTC | ACT | GCG | GAT | CAG | ATC | TTT | GTG | CAG | CTG | GAG | AAG | ATC | TGG |
| | D | G | T | P | L | T | A | D | Q | I | F | V | Q | L | E | K | I | W |
| 649 | AAC | TCA | TCC | CTA | CAG | ACC | AAG | GCA | GAG | CCT | GTG | ATC | CTC | ACC | TCC | AAC | CAC |
| | N | S | S | L | Q | T | K | A | E | P | V | I | L | T | S | N | H |
| 703 | CGC | AAC | TCC | TGG | GCC | AAG | GCA | TAC | AAC | ACC | CTC | ATC | AAA | GAC | AAG | GTG | AAC | CGG |
| | R | N | S | W | A | K | A | Y | N | T | L | I | K | D | K | V | N | R |
| 757 | GAT | TCC | GTG | CGC | ATC | CAG | AAG | AGC | TTC | ACC | GTG | TGC | CTA | GAT | GCA | ACC |
| | D | S | V | R | I | Q | K | S | F | T | V | C | L | D | A | T |
| 811 | ATG | CCC | AGG | GTC | TCA | GAA | GAC | GTG | TAC | CGC | AGC | CAC | GGC | CAG | ATG | CTG |
| | M | P | R | V | S | E | D | V | Y | R | S | H | G | Q | M | L |
| 865 | CAT | GGG | GGC | AGC | AGG | CTC | AAC | AGC | AAC | GGC | TGG | TTC | GAC | AAG | ACG | GCA |
| | H | G | G | S | R | L | N | S | N | G | W | F | D | K | T | A |
| 919 | CAG | TTC | ATC | GTG | GCA | GAA | GAT | GGC | TCC | TGT | GGG | CTT | GTG | TAC | GAG | CAT | GCT | GCA |
| | Q | F | I | V | A | E | D | G | S | C | G | L | V | Y | E | H | A | A |
| 973 | GCG | GAG | GGG | CCC | CCT | ATT | GTC | CTG | GAC | TAT | GTC | ATC | GAG | TAC | ACG | AAG |
| | A | E | G | P | P | I | V | L | D | Y | V | I | E | Y | T | K |
| 1027 | AAA | CCC | GAG | CTT | GTG | CGG | TCT | CCC | ATG | GTG | CCC | CTG | ATG | CCC | AAG | GCC | AAG | CTG |
| | K | P | E | L | V | R | S | P | M | V | P | L | M | P | K | A | K | L |
| 1081 | CGG | TTC | AAC | ATC | ACC | CCC | GAG | ATC | AAG | AGC | GAC | ATC | GAG | AAG | CAG | AAC |
| | R | F | N | I | T | P | E | I | K | S | D | I | E | K | A | K | Q | N |

MATCH WITH FIG. 1C

FIG. 1C

MATCH WITH FIG. 1B

1135  CTC AGC ATC ATG ATC CAG GAC CTG GAT ATC ACC GTG ATG GTG TTC CAC CAT TTT
       L   S   I   M   I   Q   D   L   D   I   T   V   M   V   F   H   H   F
1189  GGA AAA GAC TTC CCC AAG TCG GAG AAG CTA AGC CCA AAG GAT GCC TTC ATC CAG ATG
       G   K   D   F   P   K   S   E   K   L   S   P   K   D   A   F   I   Q   M
1243  GCT TTG CAG CTG GCC TAC TAC AGG TTC TAC GGA TTT GGG AAG TGT GCC ACC TAT GAA
       A   L   Q   L   A   Y   Y   R   F   Y   G   F   G   K   C   A   T   Y   E
1297  AGT GCC TCC CTG CGC ATG TTT CAC CTG AAG CTT GGG CGC ACC ATC CGC TCG GGT
       S   A   S   L   R   M   F   H   L   K   L   G   R   T   I   R   S   G
1351  TCC ATG GAC TCA CTC TTT GTC CTG CGG GAG ATG GAT TCC AGC GTC ACG GAG
       S   M   D   S   L   F   V   L   R   E   M   D   D   S   V   T   E
1405  CAG CAG AAG GTG GAG GGG GAG GGC ATG GCC GTG CAG CAC CAC CGA GGT TAC ACC
       H   Q   K   V   E   L   G   E   G   M   A   V   Q   H   L   G   Y   T
1459  GAC CGG GCC ATC GAG ATG TTC CGG GGC TTT GAC GAT GAT CGA GCC CTG GGG CTG AAG CTG
       D   R   A   I   E   M   F   R   G   F   D   D   R   A   L   G   L   K   L
1513  CAG GCC ATC GAG GAC ATG GTG CTC CAC AGC ATG GAC CCC ATG TTC ATG GAC ACC TAC
       Q   A   I   E   D   L   V   L   H   S   M   D   P   M   F   M   D   T   Y
1567  GCC ATC GGC TAC TTC CTC TCC GAG GTC CAG AGG GTC CCT GCC AAG ATG
       A   I   G   Y   F   L   S   E   V   Q   R   V   P   A   K   M
1621  TGT CAT GTT CTT CGG GCC CGT GGT CCC CGG GTA CGG CGG CTT TAT AAC CCC
       C   H   V   L   R   A   R   G   P   R   V   R   R   L   Y   N   P
1675  ATG GAG GGC CAC ATC AAC TTC TCC CTG TCG GAC TAC AAA AGG TGG GGG GAG ACC
       M   E   G   H   I   N   F   S   L   S   D   Y   K   R   W   G   E   T

MATCH WITH FIG. 1D

FIG. 1D

MATCH WITH FIG. 1C

```
     M   E   G   H   I   N   F   S   L   S   D   Y   K   R   W   G   E   T
1729 AAC GCC GCC CGC CTG GTG TAT TAC CTG GAG AAG GCG CTC CTG GAC ATG CGT GCC
     N   A   A   R   L   V   Y   Y   L   E   K   A   L   L   D   M   R   A
1783 CTG GTG AAG AGC CAC CCC CGG GCC TTA TTC GCC CCT AGG ACT CAG GCC TGC
     L   V   K   S   H   P   R   A   K   F   L   A   P   R   T   Q   A   C
1837 CAA TGC CAC AGG CAA GCC CAC CCT AGG ATG GGC CAC CCA CCA GGG ATC AGC TCC
     Q   C   H   R   Q   A   H   P   R   M   G   H   P   P   G   I   S   S
1891 TTG GTT CCC TCT TCC TTG GTT CCC CTG TCC CCC CCA ATT CTA CTG AGC
     L   V   P   S   S   L   V   P   L   S   P   P   I   L   L   S
1945 CAC GGA CCG CAT CCT CCA GGG TGC AGG CCC AGC CAA GTG CCT TCC GTG GGT
     H   G   P   H   P   P   G   C   R   P   S   Q   V   P   S   V   G
1999 CAT CCC AGC ACC TGC CAG GGC CCG ACC TGG GGC TGA
     H   P   S   T   C   Q   G   P   T   W   G   *
```

HUMAN CHOLINE ACETYLTRANSFERASE

This application is a continuation-in-part of and claims benefit under 35 U.S.C. § 120 to, patent application Ser. No: PCT/US94/13570, filed Nov. 23, 1994.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is choline acetyltransferase, sometimes hereinafter referred to as "hChAT". The invention also relates to inhibiting the action of such polypeptides.

A human choline acetyltransferase gene has been isolated from the human brain (McGeer P. L. et al., Life Sci., 34:2319–2338 (1984)). Choline acetyltransferase is specifically expressed in cholinergic neurons. Choline acetyltransferase is an enzyme which catalyzes a reaction which yields the neurotransmitter acetylcholine. Although choline acetyltransferase expression has been found in both neurons and certain non-neuronal tissues, such as placenta (Schuberth, J., Biochim. Biophys. Acta, 122:470–481 (1966)) and spermatozoa (Ibanez, C. F. and Persson, H., Eur. J. Neurosci., 3:1309–1315 (1991)), the expression of this enzyme is largely limited to certain neurons.

The 5' flanking region of the human choline acetyltransferase gene differs from the rodent gene in that the rodent gene has a "TATAA" box consensus sequence upstream of the transcription start site, but no such element is found in the human gene. The rodent gene also differs in that it contains at least three promoters and the sequence corresponding to only one of the promoters, the M type, is found in the human gene (Hersh, L. B., et al., J. Neurochem., 61:306–314 (1993)).

The control of motor behavior constitutes one of the most important functions of the central nervous system. Numerous regions of the brain are involved in this process that is integrated ultimately in the motor neurons of the spinal cord, the "final common path" in the control of movement. These neurons, which lie in the ventral horn, exhibit a cholinergic phenotype and, therefore, express choline acetyltransferase. Choline acetyltransferase is a specific marker of the cholinergic system.

In accordance with one aspect of the present invention, there is provided a novel mature polypeptide which is hChaT, as well as biologically active and diagnostically or therapeutically useful fragments, analogs and derivatives thereof.

In accordance with another aspect of the present invention, there are provided isolated nucleic acid molecules encoding hChaT, including mRNAs, DNAs, cDNAs, genomic DNA as well as biologically active and diagnostically or therapeutically useful fragments, analogs and derivatives thereof.

In accordance with yet a further aspect of the present invention, there is provided a process for producing such polypeptide by recombinant techniques which comprises culturing recombinant prokaryotic and/or eukaryotic host cells, containing a hChaT nucleic acid sequence, under conditions promoting expression of said protein and subsequent recovery of said protein.

In accordance with yet a further aspect of the present invention, there is provided a process for utilizing such polypeptides, or polynucleotide encoding such polypeptide for therapeutic purposes, for example, to treat amyotrophic lateral sclerosis (ALS), Alzheimer's Disease, familial disautonomia, Huntington's Disease, mental retardation, memory loss, myasthenia gravis and other disorders known to involve the cholinergic system or affect its pathways and nerves in the body.

In accordance with another aspect of the present invention there are provided nucleic acid probes comprising nucleic acid molecules of sufficient length to specifically hybridize to hChaT sequences.

In accordance with yet a further aspect of the present invention, there are provided antibodies against such polypeptides.

In accordance with another aspect of the present invention there is provided a method of diagnosing a disease or a susceptibility to a disease, related to a mutation in hChaT nucleic acid sequences and the protein encoded by such nucleic acid sequences, for example, Alzheimer's disease.

In accordance with yet another aspect of the present invention, there are provided antagonists to such polypeptides, which may be used to inhibit the action of such polypeptides, for example, in the treatment of Parkinson's Disease and accidental overdoses with various pharmaceuticals and contamination by toxins.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–D depicts the cDNA sequence (SEQ ID NO:1) and corresponding deduced amino acid sequence of hChat. The hChat polypeptide (SEQ ID NO:2) as shown is the putative mature polypeptide. The standard one-letter abbreviations for amino acids are used.

In accordance with an aspect of the present invention, there is provided an isolated nucleic acid (polynucleotide) which encodes for the mature polypeptide having the deduced amino acid sequence of FIGS. 1A–D (SEQ ID NO:2) or for the mature polypeptide encoded by the cDNA of the clone deposited as ATCC Deposit No. 75856 on Aug. 9, 1994.

The ATCC number referred to above is directed to a biological deposit with the ATCC, 10801 University Blvd., Manassas, Va. 20110-2209. Since the strain referred to is being maintained under the terms of the Budapest Treaty, it will be made available to a patent office signatory to the Budapest Treaty.

A polynucleotide encoding a polypeptide of the present invention may be obtained from fetal liver and fetal lung. The polynucleotide of this invention was discovered in a cDNA library derived from human fetal lung. It contains an open reading frame encoding a protein of 677 amino acid residues. The protein exhibits the highest degree of homology to pig choline acetyltransferase with 43% identity and 64% similarity over a 145 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–D or that of the deposited clone or may be a different coding sequence which coding sequence, as a result of the redundancy or degeneracy of the genetic code, encodes the same mature polypeptide as the DNA of FIGS. 1A–D or the deposited cDNA.

The polynucleotide which encodes for the mature polypeptide of FIG. 1 or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–D (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for a fragment, derivative or analog of the polypeptide of FIGS. 1A–D (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–D (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–D (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIGS. 1A–D (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–D (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli$.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.\ coli$, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9

(Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The hChat polypeptides of the present invention catalyze the transfer of the acyl-group to choline to yield acetylcholine. A deficiency of the neurotransmitter acetylcholine leads to cognitive and/or neurological deficiencies and/or mood or mental disturbances, such as suffering from degenerative nervous system disorders.

Accordingly, the hChat polypeptides of the present invention may be employed to treat amyotrophic lateral sclerosis, Alzheimer's Disease, senile-dementia, multi-infarct dementia, familial disautonomia, Huntington's Disease, mental retardation, memory loss and myasthenia gravis.

The hChat polypeptides may also be employed to treat disorders known to involve the cholinergic system or affect its pathways and nerves in the body. Examples of such disorders include gut and GI disorders, cord disorders, including movement, continence and sensation, stem disorders, including sleep, blood pressure, respiration, and balance, hypothalamus disorders, including temperature, respiration, and endocrine function, and limbic system disorders, including schizophrenia, memory disorders, and dementia.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors. For example, the polynucleotides and polypeptides of the present invention may be employed as research reagents and materials for discovery of treatments and diagnostics to human disease.

This invention provides a method for identification of the receptor for hChat. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to hChat, and a cDNA library created from this RNA is divided into pools and used to transfect COS cells or other cells that are not responsive to hChat. Transfected cells which are grown on glass slides are exposed to labeled hChat. hChat can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled hChat can be photoaffinity linked with cell membrane or extract preparations that express the receptor molecule. Cross-linked material is resolved by SDS-PAGE and exposed to X-ray film. The labeled complex containing the hChat-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention also provides a method of screening compounds to identify those which specifically interact with, and enhance or block, the synthesis of acetylcholine by choline acetyltransferase. An example of such a method includes incubating acetyl-CoA, choline, hChat and the potential agonist or antagonist under appropriate conditions such that hChat would normally catalyzes the transfer of the acyl-group to choline to yield acetylcholine. Results can be measured as pmol of acetylcholine formed per minute and per mg of protein. Control reactions could be performed in the absence of the agonist or antagonist such that an increased or decreased production of acetylcholine necessitates the finding of the agonist or antagonist as effective.

A potential hChaT antagonist is an antibody, or in some cases, an oligonucleotide, which binds to hChat and blocks its interaction with acetyl-CoA. Potential antagonists may also be proteins which are closely related to hChat but impart no biological functions such that the synthesis of acetylcholine is prevented, e.g., fragments of hChat.

Potential hChaT antagonists also include antisense constructs prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of hChat. The antisense RNA oligonucleotide hybridizes to the mRNA in vivo and blocks translation of the mRNA molecule into the hChat polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hChat.

A potential antagonist includes a small molecule which binds to and occupies the catalytic site of the hChat polypeptide thereby making the catalytic site inaccessible to acetyl-CoA such that synthesis of acetylcholine is prevented. Examples of small molecules include, but are not limited to, small peptides or peptide-like molecules.

The antagonists may be employed to treat Parkinson's Disease, which produces a relative excess of acetylcholine because of the loss of dopamine. Similarly, accidental overdoses with various pharmaceuticals and contamination by toxins can also produce relative over-activity of the cholinergic system and may be treated with the antagonists of the present invention.

The antagonists may be employed in a composition with a pharmaceutically acceptable carrier, e.g., as hereinafter described.

The hChat polypeptides and agonists and antagonists may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

These pharmaceutical compositions are administered in a convenient manner such as by the intravenous, intracerebral, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The hChat polypeptides, agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the hChaT gene as part of a diagnostic assay for detecting diseases or susceptibility to diseases related to the presence of mutated hChaT. Such diseases are related to an acetylcholine deficiency, for example, neurological disorders. Individuals carrying mutations in the hChaT gene may be detected at the DNA level by a variety of techniques. Nucleic acids for diagnosis may be obtained from a patient's cells, such as from blood, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding hChaT can be used to identify and analyze hChaT mutations. For example, deletions and insertions can be detected by a change in size of the amplified product in comparison to the normal genotype. Point mutations can be identified by hybridizing amplified DNA to radiolabeled hChaT RNA or alternatively, radiolabeled hChaT antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of hChat protein in various tissues since an over-expression of the proteins compared to normal control tissue samples may detect the presence of a neurological disease or susceptibility to a neurological disease. Assays used to detect levels of hChat protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the hChat antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any hChat proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to hChat. Unattached reporter antibody is then washed out. Peroxidase substrates are then added to the dish and the amount of color developed in a given time period is a measurement of the amount of hChat protein present in a given volume of patient sample when compared against a standard curve.

A competition assay may be employed wherein antibodies specific to hChat are attached to a solid support and labeled hChat and a sample derived from the host are passed over the solid support and the amount of label detected, for example by liquid scintillation chromatography, can be correlated to a quantity of hChat in the sample.

A "sandwich" assay is similar to an ELISA assay. In a "sandwich" assay hChat is passed over a solid support and binds to antibody attached to a solid support. A second antibody is then bound to the hChat. A third antibody which is labeled and specific to the second antibody is then passed over the solid support and binds to the second antibody and an amount can then be quantitated.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements are used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of hChat

The DNA sequence encoding hChat, ATCC # 75856, is initially amplified using PCR oligonucleotide primers corresponding to the 5' and sequences of the processed hChat protein (minus the signal peptide sequence) and the vector sequences 3' to the hChat gene. Additional nucleotides corresponding to hChat are added to the 5' and 3' sequences respectively. The 5' oligonucleotide primer has the sequence 5' CGCG<u>AGATCC</u>ACCATGAAGGCTTCCAGCCGCTTC 3' (SEQ ID No. 3) contains a BamHI restriction enzyme site (underlined) followed by 21 nucleotides of hChat coding sequence starting from the presumed terminal amino acid of the processed protein codon. The 3' sequence 5' CGCG <u>TCTAGA</u>AGGGTACAGATGGTG GCC 3' (SEQ ID No. 4) contains complementary sequences to an XbaI site (underlined) and is followed by 18 nucleotides of hChat noncoding sequence located 3' to the hChat DNA insert. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with BamHI and XbaI. The amplified sequences are ligated into pQE-9 and are inserted in frame with the sequence encoding for the histidine tag and the RBS. The ligation mixture is then used to transform E. coli strain m15/REP4 available from Qiagen by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized hChat is purified from this solution by chromatography on a Nickel-Chelate column under conditions that allow for tight binding by proteins containing the 6-His tag (Hochuli, E. et al., J. Chromatography 411:177–184 (1984)). hChat is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2

Cloning and Expression of hChat Using the Baculovirus Expression System

The DNA sequence encoding the full length hChat protein, ATCC # 75856, is amplified using PCR oligonucleotide primers corresponding to the 5' and 3' sequences of the gene:

The 5' primer has the sequence 5' CGCGGGATCCAC-CATGAAGGCTTCCAGCCGCTTC 3' (SEQ ID No. 5) and contains a Bam H1 restriction enzyme site (in bold) followed by 3 non-specific nucleotides and 21 nucleotides encoding hChat which resembles an efficient signal for the initiation of translation in eukaryotic cells (J. Mol. Biol. 1987, 196, 947–950, Kozak, M.).

The 3' primer has the sequence 5' CGCGGGTACCAG-GTACAGATGGTGGCC 3' (SEQ ID No. 6) and contains the cleavage site for the restriction endonuclease Asp718 (in bold) followed by 16 nucleotides complementary to the coding region of hChat. The amplified sequences are isolated from a 1% agarose gel using a commercially available kit ("Geneclean," BIO 101 Inc., La Jolla, Calif.). The fragment is then digested with the endonucleases Bam H1 and Asp718 and then purified as described above. This fragment is designated F2.

The vector pA35 (modification of pVL941 vector, discussed below) is used for the expression of the hChat protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases Bam H1 and Asp718. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pRG1, pAc373, pVL941 and pAcIM1 (Luckow, V. A. and Summers, M. D., Virology, 170:31–39).

The plasmid is digested with the restriction enzymes Bam H1 and Asp718 and then dephosphorylated using calf intestinal phosphatase by procedures known in the art. The DNA is then isolated from a 1% agarose gel as described in Example 1. This vector DNA is designated V2.

Fragment F2 and the dephosphorylated plasmid V2 are ligated with T4 DNA ligase. *E. coli* HB101 cells are then transformed and bacteria identified that contained the plasmid (pBac hChat) with the hChat gene using the enzymes Bam H1 and Asp718. The sequence of the cloned fragment is confirmed by DNA sequencing.

5 μg of the plasmid pBac hChat are cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac hChat are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses is added to the cells, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-hChat at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant hChat in COS Cells

The expression of plasmid, hChat HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire hChat precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding hChat, ATCC# 75856, is constructed by PCR on the original EST cloned using two primers: the 5' primer 5' CGCGGGATCCACCATGAAG-GCTTCCAGCCGCTTC 3' (SEQ ID No. 7) contains a Bam H1 site (bold) followed by 21 nucleotides of hChat coding sequence starting from the initiation codon; the 3' sequence 5' CGCGTCTAGATCAAG CGTAGTCTGGGACGTCG-TATGGGTAGCCTCTGCACTCAGCCCC 3' (SEQ ID No. 8) contains complementary sequences to an Xba I site (bold), translation stop codon, HA tag and the last 18 nucleotides of the hChat coding sequence (not including the stop codon). Therefore, the PCR product contains a Bam H1 site, hChat coding sequence followed by HA tag fused in frame, a translation termination stop codon next to the HA tag, and an Xba I site. The PCR amplified DNA fragment and the vector, pcDNAI/Amp, are digested with Bam H1 and Xba I restriction enzyme and ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant hChat, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the hChat HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid sequence selected from the group consisting of:
   (a) a nucleic acid sequence encoding the polypeptide set forth as amino acid residues 1 to 677 of SEQ ID NO:2;
   (b) a nucleic acid sequence encoding the polypeptide set forth as amino acid residues 2 to 677 of SEQ ID NO:2;
   (c) a nucleic acid sequence encoding the polypeptide set forth as amino acid residues 2 to 677, wherein said polypeptide has at least one conservative amino acid substitution, and further wherein said polypeptide retains enzymatic activity;
   (d) a nucleic acid sequence encoding a fragment of the polypeptide set forth as amino acid residues 1 to 677 of SEQ ID NO:2, wherein said polypeptide fragment has enzymatic activity;
   (e) a nucleic acid sequence encoding at least 30 contiguous amino acid residues of SEQ ID NO:2, wherein said amino acid residues bind an antibody which binds specifically to SEQ ID NO:2; and
   (f) a nucleic acid sequence complementary to the nucleic acid sequence of (a), (b), (c), (d) or (e).

2. The isolated polynucleotide of claim 1, wherein said nucleic acid sequence is (a).

3. The isolated polynucleotide of claim 1, wherein said nucleic acid sequence is (b).

4. The isolated polynucleotide of claim 1, wherein said nucleic acid sequence is (c).

5. The isolated polynucleotide of claim 1, wherein said nucleic acid sequence is (d).

6. The isolated polynucleotide of claim 1, wherein said nucleic acid sequence is (e).

7. The isolated polynucleotide of claim 1, wherein said nucleic acid sequence is (f).

8. The isolated polynucleotide of claim 1, wherein said polynucleotide is DNA.

9. An isolated polynucleotide comprising the polynucleotide of claim 1 fused to a heterologous polynucleotide.

10. The isolated polynucleotide of claim 9, wherein said isolated polynucleotide encodes a heterologous polypeptide.

11. The isolated polynucleotide of claim 1 operably associated with a regulatory sequence that controls gene expression.

12. An isolated vector comprising the polynucleotide of claim 1.

13. An isolated recombinant host cell transformed or transfected with the polynucleotide of claim 1, wherein the nucleic acid sequence is (a), (b), (c), (d) or (e).

14. A method for producing a polypeptide, comprising:
   (a) culturing the recombinant host cell of claim 13 under conditions suitable to produce the polypeptide; and
   (b) recovering the polypeptide from the cell culture.

15. The isolated polynucleotide of claim 1 consisting of a nucleic acid sequence selected from the group consisting of:
   (a) a nucleic acid sequence encoding the polypeptide set forth as amino acid residues 1 to 677 of SEQ ID NO:2;
   (b) a nucleic acid sequence encoding the polypeptide set forth as amino acid residues 2 to 677 of SEQ ID NO:2;
   (c) a nucleic acid sequence encoding the polypeptide set forth as amino acid residues 2 to 677, wherein said polypeptide has at least one conservative amino acid substitution, and further wherein said polypeptide retains enzymatic activity;
   (d) a nucleic acid sequence encoding a fragment of the polypeptide set forth as amino acid residues 1 to 677 of SEQ ID NO:2, wherein said polypeptide fragment has enzymatic activity;
   (e) a nucleic acid sequence encoding at least 30 contiguous amino acid residues of SEQ ID NO:2; and
   (f) a nucleic acid sequence complementary to the nucleic acid sequence of (a), (b), (c), (d) or (e).

16. The isolated polynucleotide of claim 15, wherein said nucleic acid sequence is (a).

17. The isolated polynucleotide of claim 15, wherein said nucleic acid sequence is (b).

18. The isolated polynucleotide of claim 15, wherein said nucleic acid sequence is (c).

19. The isolated polynucleotide of claim 15, wherein said nucleic acid sequence is (d).

20. The isolated polynucleotide of claim 15, wherein said nucleic acid sequence is (e).

21. The isolated polynucleotide of claim 15, wherein said nucleic acid sequence is (f).

22. The isolated polynucleotide of claim 15, wherein said polynucleotide is DNA.

23. An isolated polynucleotide comprising the polynucleotide of claim 15 fused to a heterologous polynucleotide.

24. The isolated polynucleotide of claim 23, wherein said isolated polynucleotide encodes a heterologous polypeptide.

25. The isolated polynucleotide of claim 15 operably associated with a regulatory sequence that controls gene expression.

26. An isolated vector comprising the polynucleotide of claim 15.

27. An isolated recombinant host cell transformed or transfected with the polynucleotide of claim 15, wherein the nucleic acid sequence is (a), (b), (c), (d) or (e).

28. A method for producing a polypeptide, comprising:
(a) culturing the recombinant host cell of claim 27 under conditions suitable to produce the polypeptide; and
(b) recovering the polypeptide from the cell culture.

29. An isolated polynucleotide comprising a nucleic acid sequence selected from the group consisting of:
(a) a nucleic acid sequence encoding the full-length polypeptide encoded by the human cDNA contained in ATCC Deposit No. 75856;
(b) a nucleic acid sequence encoding the full-length polypeptide encoded by the human cDNA contained in ATCC Deposit No. 75856, excepting the N-terminal methionine;
(c) a nucleic acid sequence encoding the full-length polypeptide encoded by the human cDNA contained in ATCC Deposit No. 75856, excepting the N-terminal methionine, wherein said nucleic acid sequence encodes a polypeptide containing at least one conservative amino acid substitution, and further wherein said polypeptide has enzymatic activity;
(d) a nucleic acid sequence encoding a fragment of the polypeptide encoded by the human cDNA contained in ATCC Deposit No. 75856, wherein said polypeptide fragment has enzymatic activity;
(e) a nucleic acid sequence encoding at least 30 contiguous amino acid residues of the polypeptide encoded by the human cDNA contained in ATCC Deposit No. 75856, wherein said amino acid residues bind an antibody which binds specifically to the polypeptide encoded by the human cDNA contained in ATCC Deposit No. 75856; and
(f) a nucleic acid sequence complementary to the nucleic acid sequence of (a), (b), (c), (d) or (e).

30. The isolated polynucleotide of claim 29, wherein said nucleic acid sequence is (a).

31. The isolated polynucleotide of claim 29, wherein said nucleic acid sequence is (b).

32. The isolated polynucleotide of claim 29, wherein said nucleic acid sequence is (c).

33. The isolated polynucleotide of claim 29, wherein said nucleic acid sequence is (d).

34. The isolated polynucleotide of claim 29, wherein said nucleic acid sequence is (e).

35. The isolated polynucleotide of claim 29, wherein said nucleic acid sequence is (f).

36. The isolated polynucleotide of claim 29, wherein said polynucleotide is DNA.

37. An isolated polynucleotide comprising the polynucleotide of claim 29 fused to a heterologous polynucleotide.

38. The isolated polynucleotide of claim 37, wherein said isolated polynucleotide encodes a heterologous polypeptide.

39. The isolated polynucleotide of claim 29 operably associated with a regulatory sequence that controls gene expression.

40. An isolated vector comprising the polynucleotide of claim 29.

41. An isolated recombinant host cell transformed or transfected with the polynucleotide of claim 29, wherein the nucleic acid sequence is (a), (b), (c), (d) or (e).

42. A method for producing a polypeptide, comprising:
(a) culturing the recombinant host cell of claim 41 under conditions suitable to produce the polypeptide; and
(b) recovering the polypeptide from the cell culture.

43. The isolated polynucleotide of claim 29 consisting of a nucleic acid sequence selected from the group consisting of:
(a) a nucleic acid sequence encoding the full-length polypeptide encoded by the human cDNA contained in ATCC Deposit No. 75856;
(b) a nucleic acid sequence encoding the full-length polypeptide encoded by the human cDNA contained in ATCC Deposit No. 75856, excepting the N-terminal methionine;
(c) a nucleic acid sequence encoding the full-length polypeptide encoded by the human cDNA contained in ATCC Deposit No. 75856, excepting the N-terminal methionine, wherein said nucleic acid sequence encodes a polypeptide containing at least one conservative amino acid substitution, and further wherein said polypeptide has enzymatic activity;
(d) a nucleic acid sequence encoding a fragment of the polypeptide encoded by the human cDNA contained in ATCC Deposit No. 75856, wherein said polypeptide fragment has enzymatic activity;
(e) a nucleic acid sequence encoding a fragment of the polypeptide encoded by the nucleic acid of (a), wherein said polypeptide fragment has enzymatic activity;
(f) a nucleic acid sequence complementary to the nucleic acid sequence of (a), (b), (c), (d) or (e).

44. The isolated polynucleotide of claim 43, wherein said nucleic acid sequence is (a).

45. The isolated polynucleotide of claim 43, wherein said nucleic acid sequence is (b).

46. The isolated polynucleotide of claim 43, wherein said nucleic acid sequence is (c).

47. The isolated polynucleotide of claim 43, wherein said nucleic acid sequence is (d).

48. The isolated polynucleotide of claim 43, wherein said nucleic acid sequence is (e).

49. The isolated polynucleotide of claim 43, wherein said nucleic acid sequence is (f).

50. The isolated polynucleotide of claim 43, wherein said polynucleotide is DNA.

51. An isolated polynucleotide comprising the polynucleotide of claim 43 fused to a heterologous polynucleotide.

52. The isolated polynucleotide of claim 51, wherein said isolated polynucleotide encodes a heterologous polypeptide.

53. The isolated polynucleotide of claim 43 operably associated with a regulatory sequence that controls gene expression.

54. An isolated vector comprising the polynucleotide of claim 43.

55. An isolated recombinant host cell transformed or transfected with the polynucleotide of claim 43, wherein the nucleic acid sequence is (a), (b), (c), (d) or (e).

56. A method for producing a polypeptide, comprising:
(a) culturing the recombinant host cell of claim 55 under conditions suitable to produce the polypeptide; and
(b) recovering the polypeptide from the cell culture.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2034 base pairs
      (B) TYPE: nucleic acid

```
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..2031

(xi) SEQUENCE DESCRIPTION: SEQ ID NO:1:

ATG AAG GCT TCC AGC CGC TTC AAG GCA CAC CAG GAT GCA CTG CCA CGG          48
Met Lys Ala Ser Ser Arg Phe Lys Ala His Gln Asp Ala Leu Pro Arg
 1               5                  10                  15

TTG CCC GTG CCC CCT CTC CAG CAG TCC CTG GAC CAC TAC CTG AAG GCG          96
Leu Pro Val Pro Pro Leu Gln Gln Ser Leu Asp His Tyr Leu Lys Ala
                20                  25                  30

CTG CAG CCC ATC GTG AGT GAG GAG GAG TGG GCC CAC ACC AAG CAG CTG         144
Leu Gln Pro Ile Val Ser Glu Glu Glu Trp Ala His Thr Lys Gln Leu
            35                  40                  45

GTG GAT GAG TTT CAG GCC TCA GGA GGT GTA GGG GAG CGC CTG CAG AAG         192
Val Asp Glu Phe Gln Ala Ser Gly Gly Val Gly Glu Arg Leu Gln Lys
 50                  55                  60

GGG CTG GAG CGT CGG GCC AGG AAG ACG GAG AAC TGG CTG TCT GAG TGG         240
Gly Leu Glu Arg Arg Ala Arg Lys Thr Glu Asn Trp Leu Ser Glu Trp
 65                  70                  75                  80

TGG CTC AAG ACC GCC TAC CTC CAG TAC CGC CAG CCT GTG GTC ATC TAC         288
Trp Leu Lys Thr Ala Tyr Leu Gln Tyr Arg Gln Pro Val Val Ile Tyr
                85                  90                  95

TCG AGC CCA GGC GTG ATG CTA CCC AAG CAG GAC TTC GTG GAC CTG CAG         336
Ser Ser Pro Gly Val Met Leu Pro Lys Gln Asp Phe Val Asp Leu Gln
               100                 105                 110

GGT CAG CTC CGA TTT GCT GCC AAA CTC ATT GAG GGT GTG TTG GTT TTC         384
Gly Gln Leu Arg Phe Ala Ala Lys Leu Ile Glu Gly Val Leu Val Phe
            115                 120                 125

AAG GTC ATG ATT GAC AAC GAG ACC CTG CCC GTG GAG TAC CTG GGG GGG         432
Lys Val Met Ile Asp Asn Glu Thr Leu Pro Val Glu Tyr Leu Gly Gly
130                 135                 140

AAG CCA CTG TGC ATG AAC CAG TTC TAT CAG ATC TTG TCC TCC TGC CGA         480
Lys Pro Leu Cys Met Asn Gln Phe Tyr Gln Ile Leu Ser Ser Cys Arg
145                 150                 155                 160

GTG CCG GGC CCC AAG CAG GAC ACA GTC AGC AAC TTC AGC AAG ACC AAG         528
Val Pro Gly Pro Lys Gln Asp Thr Val Ser Asn Phe Ser Lys Thr Lys
                165                 170                 175

AAG CCT CCC ACG CAC ATC ACC GTG GTA CAC AAC TAC CAG TTT TTT GAG         576
Lys Pro Pro Thr His Ile Thr Val Val His Asn Tyr Gln Phe Phe Glu
            180                 185                 190

CTG GAT GTG TAC CAC AGT GAC GGG ACA CCC CTC ACT GCG GAT CAG ATC         624
Leu Asp Val Tyr His Ser Asp Gly Thr Pro Leu Thr Ala Asp Gln Ile
        195                 200                 205

TTT GTG CAG CTG GAG AAG ATC TGG AAC TCA TCC CTA CAG ACC AAC AAG         672
Phe Val Gln Leu Glu Lys Ile Trp Asn Ser Ser Leu Gln Thr Asn Lys
210                 215                 220

GAG CCT GTG GGC ATC CTC ACC TCC AAC CAC CGC AAC TCC TGG GCC AAG         720
Glu Pro Val Gly Ile Leu Thr Ser Asn His Arg Asn Ser Trp Ala Lys
225                 230                 235                 240

GCA TAC AAC ACC CTC ATC AAA GAC AAG GTG AAC CGG GAT TCC GTG CGC         768
Ala Tyr Asn Thr Leu Ile Lys Asp Lys Val Asn Arg Asp Ser Val Arg
                245                 250                 255

TCC ATC CAG AAG AGC ATC TTC ACC GTG TGC CTA GAT GCA ACC ATG CCC         816
Ser Ile Gln Lys Ser Ile Phe Thr Val Cys Leu Asp Ala Thr Met Pro
            260                 265                 270
```

```
AGG GTC TCA GAA GAC GTG TAC CGC AGC CAC GTG GCA GGC CAG ATG CTG        864
Arg Val Ser Glu Asp Val Tyr Arg Ser His Val Ala Gly Gln Met Leu
        275                 280                 285

CAT GGG GGC GGC AGC AGG CTC AAC AGC GGC AAC CGC TGG TTC GAC AAG        912
His Gly Gly Gly Ser Arg Leu Asn Ser Gly Asn Arg Trp Phe Asp Lys
        290                 295                 300

ACG CTG CAG TTC ATC GTG GCA GAA GAT GGC TCC TGT GGG CTT GTG TAC        960
Thr Leu Gln Phe Ile Val Ala Glu Asp Gly Ser Cys Gly Leu Val Tyr
305                 310                 315                 320

GAG CAT GCT GCA GCG GAG GGG CCC CCT ATT GTC ACC CTT CTG GAC TAT       1008
Glu His Ala Ala Ala Glu Gly Pro Pro Ile Val Thr Leu Leu Asp Tyr
                325                 330                 335

GTC ATC GAG TAC ACG AAG AAA CCC GAG CTT GTG CGG TCT CCC ATG GTG       1056
Val Ile Glu Tyr Thr Lys Lys Pro Glu Leu Val Arg Ser Pro Met Val
            340                 345                 350

CCC CTG CCC ATG CCC AAG AAG CTG CGG TTC AAC ATC ACC CCC GAG ATC       1104
Pro Leu Pro Met Pro Lys Lys Leu Arg Phe Asn Ile Thr Pro Glu Ile
        355                 360                 365

AAG AGC GAC ATC GAG AAG GCC AAG CAG AAC CTC AGC ATC ATG ATC CAG       1152
Lys Ser Asp Ile Glu Lys Ala Lys Gln Asn Leu Ser Ile Met Ile Gln
        370                 375                 380

GAC CTG GAT ATC ACC GTG ATG GTG TTC CAC CAT TTT GGA AAA GAC TTC       1200
Asp Leu Asp Ile Thr Val Met Val Phe His His Phe Gly Lys Asp Phe
385                 390                 395                 400

CCC AAG TCG GAG AAG CTA AGC CCA GAT GCC TTC ATC CAG ATG GCT TTG       1248
Pro Lys Ser Glu Lys Leu Ser Pro Asp Ala Phe Ile Gln Met Ala Leu
                405                 410                 415

CAG CTG GCC TAC TAC AGG TTC TAC GGA AAG GAA TGT GCC ACC TAT GAA       1296
Gln Leu Ala Tyr Tyr Arg Phe Tyr Gly Lys Glu Cys Ala Thr Tyr Glu
            420                 425                 430

AGT GCC TCC CTG CGC ATG TTT CAC CTG GGG CGC ACC GAC ACC ATC CGC       1344
Ser Ala Ser Leu Arg Met Phe His Leu Gly Arg Thr Asp Thr Ile Arg
        435                 440                 445

TCG GGT TCC ATG GAC TCA CTC ACC TTT GTC AAG GCC ATG GAT GAC TCC       1392
Ser Gly Ser Met Asp Ser Leu Thr Phe Val Lys Ala Met Asp Asp Ser
        450                 455                 460

AGC GTC ACG GAG CAC CAG AAG GTG GAG CTG CTG CGG AAG GCC GTG CAG       1440
Ser Val Thr Glu His Gln Lys Val Glu Leu Leu Arg Lys Ala Val Gln
465                 470                 475                 480

GCC CAC CGA GGT TAC ACC GAC CGG GCC ATC CGG GGG GAG GGC TTT GAT       1488
Ala His Arg Gly Tyr Thr Asp Arg Ala Ile Arg Gly Glu Gly Phe Asp
                485                 490                 495

CGA CAC CTG CTG GGC CTG AAG CTG CAG GCC ATC GAG GAC CTG GTG AGC       1536
Arg His Leu Leu Gly Leu Lys Leu Gln Ala Ile Glu Asp Leu Val Ser
            500                 505                 510

ATG CCC GAC ATC TTC ATG GAC ACC TCC TAC GCC ATC GGC ATG TAC TTC       1584
Met Pro Asp Ile Phe Met Asp Thr Ser Tyr Ala Ile Gly Met Tyr Phe
        515                 520                 525

CAC CTC TCC ACC AGG CAG GTC CCT GCC AAG AAG ATG TGT CAT GTT CTT       1632
His Leu Ser Thr Arg Gln Val Pro Ala Lys Lys Met Cys His Val Leu
        530                 535                 540

CGG GCC CGT GGT CCC CGA CGG GTA CGG TGT CTT TAT AAC CCC ATG GAG       1680
Arg Ala Arg Gly Pro Arg Arg Val Arg Cys Leu Tyr Asn Pro Met Glu
545                 550                 555                 560

GGC CAC ATC AAC TTC TCC CTG TCG GAC TAC AAA AGG TGG GGG GAG ACC       1728
Gly His Ile Asn Phe Ser Leu Ser Asp Tyr Lys Arg Trp Gly Glu Thr
                565                 570                 575

AAC GCC GCC CGC CTG GTG TAT TAC CTG GAG AAG GCG CTC CTG GAC ATG       1776
Asn Ala Ala Arg Leu Val Tyr Tyr Leu Glu Lys Ala Leu Leu Asp Met
            580                 585                 590
```

```
CGT GCC CTG GTG AAG AGC CAC CCC CGG GCC AAG TTC TTA GCC CCT AGG      1824
Arg Ala Leu Val Lys Ser His Pro Arg Ala Lys Phe Leu Ala Pro Arg
        595                 600                 605

ACT CAG GCC TGC CAA TGC CAC AGG CAA GCC CAC CCT AGG ATG GGC CAC      1872
Thr Gln Ala Cys Gln Cys His Arg Gln Ala His Pro Arg Met Gly His
            610                 615                 620

CCA CCA GGG ATC AGC TCC TTG GTT CCC TCT TCC TTG GTT CCC TCT TCC      1920
Pro Pro Gly Ile Ser Ser Leu Val Pro Ser Ser Leu Val Pro Ser Ser
625                 630                 635                 640

CTG GTC CCC CCA ATT CTA CTG AGC CAC GGA CCG CAT CCT CCA GGG GGC      1968
Leu Val Pro Pro Ile Leu Leu Ser His Gly Pro His Pro Pro Gly Gly
                    645                 650                 655

TGC AGG CCC AGC CAA GTG CCT TCC GTG GGT CAT CCC AGC ACC TGC CAG      2016
Cys Arg Pro Ser Gln Val Pro Ser Val Gly His Pro Ser Thr Cys Gln
                660                 665                 670

GGC CCG ACC TGG GGC TGA                                              2034
Gly Pro Thr Trp Gly
        675
```

(2) INFORMATION FOR SEQ ID NO:2:

(i) SEQUENCE CHARACTERISTICS:
        (A) LENGTH: 677 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ala Ser Ser Arg Phe Lys Ala His Gln Asp Ala Leu Pro Arg
1               5                   10                  15

Leu Pro Val Pro Pro Leu Gln Gln Ser Leu Asp His Tyr Leu Lys Ala
            20                  25                  30

Leu Gln Pro Ile Val Ser Glu Glu Trp Ala His Thr Lys Gln Leu
        35                  40                  45

Val Asp Glu Phe Gln Ala Ser Gly Gly Val Gly Glu Arg Leu Gln Lys
    50                  55                  60

Gly Leu Glu Arg Arg Ala Arg Lys Thr Glu Asn Trp Leu Ser Glu Trp
65                  70                  75                  80

Trp Leu Lys Thr Ala Tyr Leu Gln Tyr Arg Gln Pro Val Val Ile Tyr
                85                  90                  95

Ser Ser Pro Gly Val Met Leu Pro Lys Gln Asp Phe Val Asp Leu Gln
            100                 105                 110

Gly Gln Leu Arg Phe Ala Ala Lys Leu Ile Glu Gly Val Leu Val Phe
        115                 120                 125

Lys Val Met Ile Asp Asn Glu Thr Leu Pro Val Glu Tyr Leu Gly Gly
    130                 135                 140

Lys Pro Leu Cys Met Asn Gln Phe Tyr Gln Ile Leu Ser Ser Cys Arg
145                 150                 155                 160

Val Pro Gly Pro Lys Gln Asp Thr Val Ser Asn Phe Ser Lys Thr Lys
                165                 170                 175

Lys Pro Pro Thr His Ile Thr Val Val His Asn Tyr Gln Phe Phe Glu
            180                 185                 190

Leu Asp Val Tyr His Ser Asp Gly Thr Pro Leu Thr Ala Asp Gln Ile
        195                 200                 205

Phe Val Gln Leu Glu Lys Ile Trp Asn Ser Ser Leu Gln Thr Asn Lys
    210                 215                 220
```

```
Glu Pro Val Gly Ile Leu Thr Ser Asn His Arg Asn Ser Trp Ala Lys
225                 230                 235                 240

Ala Tyr Asn Thr Leu Ile Lys Asp Lys Val Asn Arg Asp Ser Val Arg
            245                 250                 255

Ser Ile Gln Lys Ser Ile Phe Thr Val Cys Leu Asp Ala Thr Met Pro
        260                 265                 270

Arg Val Ser Glu Asp Val Tyr Arg Ser His Val Ala Gly Gln Met Leu
    275                 280                 285

His Gly Gly Ser Arg Leu Asn Ser Gly Asn Arg Trp Phe Asp Lys
290                 295                 300

Thr Leu Gln Phe Ile Val Ala Glu Asp Gly Ser Cys Gly Leu Val Tyr
305                 310                 315                 320

Glu His Ala Ala Ala Glu Gly Pro Pro Ile Val Thr Leu Leu Asp Tyr
            325                 330                 335

Val Ile Glu Tyr Thr Lys Lys Pro Glu Leu Val Arg Ser Pro Met Val
            340                 345                 350

Pro Leu Pro Met Pro Lys Lys Leu Arg Phe Asn Ile Thr Pro Glu Ile
        355                 360                 365

Lys Ser Asp Ile Glu Lys Ala Lys Gln Asn Leu Ser Ile Met Ile Gln
    370                 375                 380

Asp Leu Asp Ile Thr Val Met Val Phe His His Phe Gly Lys Asp Phe
385                 390                 395                 400

Pro Lys Ser Glu Lys Leu Ser Pro Asp Ala Phe Ile Gln Met Ala Leu
            405                 410                 415

Gln Leu Ala Tyr Tyr Arg Phe Tyr Gly Lys Glu Cys Ala Thr Tyr Glu
            420                 425                 430

Ser Ala Ser Leu Arg Met Phe His Leu Gly Arg Thr Asp Thr Ile Arg
        435                 440                 445

Ser Gly Ser Met Asp Ser Leu Thr Phe Val Lys Ala Met Asp Asp Ser
450                 455                 460

Ser Val Thr Glu His Gln Lys Val Glu Leu Leu Arg Lys Ala Val Gln
465                 470                 475                 480

Ala His Arg Gly Tyr Thr Asp Arg Ala Ile Arg Gly Glu Gly Phe Asp
            485                 490                 495

Arg His Leu Leu Gly Leu Lys Leu Gln Ala Ile Glu Asp Leu Val Ser
        500                 505                 510

Met Pro Asp Ile Phe Met Asp Thr Ser Tyr Ala Ile Gly Met Tyr Phe
    515                 520                 525

His Leu Ser Thr Arg Gln Val Pro Ala Lys Lys Met Cys His Val Leu
530                 535                 540

Arg Ala Arg Gly Pro Arg Val Arg Cys Leu Tyr Asn Pro Met Glu
545                 550                 555                 560

Gly His Ile Asn Phe Ser Leu Ser Asp Tyr Lys Arg Trp Gly Glu Thr
            565                 570                 575

Asn Ala Ala Arg Leu Val Tyr Tyr Leu Glu Lys Ala Leu Leu Asp Met
            580                 585                 590

Arg Ala Leu Val Lys Ser His Pro Arg Ala Lys Phe Leu Ala Pro Arg
        595                 600                 605

Thr Gln Ala Cys Gln Cys His Arg Gln Ala His Pro Arg Met Gly His
    610                 615                 620

Pro Pro Gly Ile Ser Ser Leu Val Pro Ser Ser Leu Val Pro Ser Ser
625                 630                 635                 640

Leu Val Pro Pro Ile Leu Leu Ser His Gly Pro His Pro Pro Gly Gly
```

```
                   645                 650                 655
Cys Arg Pro Ser Gln Val Pro Ser Val Gly His Pro Ser Thr Cys Gln
            660                 665                 670
Gly Pro Thr Trp Gly
        675
```

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

CGCGAGATCC ACCATGAAGG CTTCCAGCCG CTTC                            34

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CGCGTCTAGA AGGGTACAGA TGGTGGCC                                  28

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CGCGGGATCC ACCATGAAGG CTTCCAGCCG CTTC                            34

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CGCGGGTACC AGGTACAGAT GGTGGCC                                   27

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA -continued (xi) SEQUENCE DESCRIPTION: SEQ ID NO:7:

CGCGGGATCC ACCATGAAGG CTTCCAGCCG CTTC        34

(2) INFORMATION FOR SEQ ID NO:8:

(i) SEQUENCE CHARACTERISTICS:
      (A) LENGTH: 58 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:8:

CGCGTCTAGA TCAAGCGTAG TCTGGGACGT CGTATGGGTA GCCTCTGCAC TCAGCCCC        58